US012629334B2

(12) United States Patent
Weinberg et al.

(10) Patent No.: US 12,629,334 B2
(45) Date of Patent: \*May 19, 2026

(54) LIPID EMULSIONS AND USES THEREOF

(71) Applicant: ResQ Pharma, Inc., Chicago, IL (US)

(72) Inventors: Guy Weinberg, Chicago, IL (US); Christopher Piers Bryant, Chicago, IL (US)

(73) Assignees: ResQ Pharma, Inc., Chicago, IL (US); The United States Government as Represented by The Department of Veterans Affairs, Washington, DC (US)

( \* ) Notice: Subject to any disclaimer, the term of this patent is extended or adjusted under 35 U.S.C. 154(b) by 115 days.

This patent is subject to a terminal disclaimer.

(21) Appl. No.: 18/093,554

(22) Filed: Jan. 5, 2023

(65) Prior Publication Data

US 2023/0148431 A1 May 11, 2023

Related U.S. Application Data

(62) Division of application No. 17/058,545, filed as application No. PCT/US2019/033997 on May 24, 2019, now abandoned.

(60) Provisional application No. 62/676,850, filed on May 25, 2018, provisional application No. 62/803,932, filed on Feb. 11, 2019, provisional application No. 62/836,394, filed on Apr. 19, 2019.

(51) Int. Cl.
| | |
|---|---|
| *A61K 9/107* | (2006.01) |
| *A61K 9/00* | (2006.01) |
| *A61P 9/04* | (2006.01) |
| *A61P 39/02* | (2006.01) |

(52) U.S. Cl.
CPC .......... *A61K 9/1075* (2013.01); *A61K 9/0019* (2013.01); *A61P 9/04* (2018.01); *A61P 39/02* (2018.01)

(58) Field of Classification Search
None
See application file for complete search history.

(56) References Cited

U.S. PATENT DOCUMENTS

| | | | |
|---|---|---|---|
| 4,878,903 A | 11/1989 | Mueller | |
| 5,478,860 A | 12/1995 | Wheeler et al. | |
| 5,542,935 A | 8/1996 | Unger et al. | |
| 5,961,970 A * | 10/1999 | Lowell ................ | A61K 9/1075 |
| | | | 424/283.1 |
| 6,074,560 A | 6/2000 | Mueller | |
| 7,261,903 B1 | 8/2007 | Weinberg et al. | |
| 8,834,919 B2 | 9/2014 | Weinberg et al. | |
| 10,716,756 B2 | 7/2020 | Simpkins | |
| 2005/0142189 A1 | 6/2005 | Lambert et al. | |
| 2008/0021411 A1 * | 1/2008 | Weinberg ............... | A61P 39/02 |
| | | | 604/218 |

FOREIGN PATENT DOCUMENTS

| | | |
|---|---|---|
| JP | 2007167576 A | 7/2007 |
| WO | 2017083780 A1 | 5/2017 |

OTHER PUBLICATIONS

APSF (APSF Newsletter. Vol. 24, No. 1, p. 1-24 (2009) (Year: 2009).*
HORIBA (2017) (Year: 2017).*
Dillon et al (Large surface area activated charcoal and the inhibition of aspirin absorption. Ann Emerg Med. May 1989; 18(5):547-52) (Year: 1989).*
Olson (Activated Charcoal for Acute Poisoning: One Toxicologist's Journey. J. Med. Toxicol. (2010) 6:190-198). (Year: 2010).*
Office Action in U.S. Appl. No. 17/058,545 mailed Mar. 14, 2023, 10 pages.
International Search Report and Written Opinion for PCT/US2019/033997, dated Sep. 30, 2019, 10 pages.
International Search Report and Written Opinion for PCT/US2019/033999, dated Aug. 12, 2019, 7 pages.
Extended European Search Report for related EP Application No. 198082193.0 dated Feb. 8, 2022, 8 pages.
Office Action in U.S. Appl. No. 17/058,545, filed Sep. 8, 2023, 20 pages.
Chemistry (Royal Society of Chemistry 2014) (Year: 2014).
Nutrilipid 20% label, Aug. 2014.

* cited by examiner

*Primary Examiner* — Jake M Vu

(74) *Attorney, Agent, or Firm* — POLSINELLI PC

(57) ABSTRACT

The present disclosure provides lipid emulsions comprising at least 20 percent (w/v) lipid with an average particle size of about 200 to about 300 nm, and use thereof to treat subjects in need of lipid emulsion therapy.

23 Claims, 6 Drawing Sheets

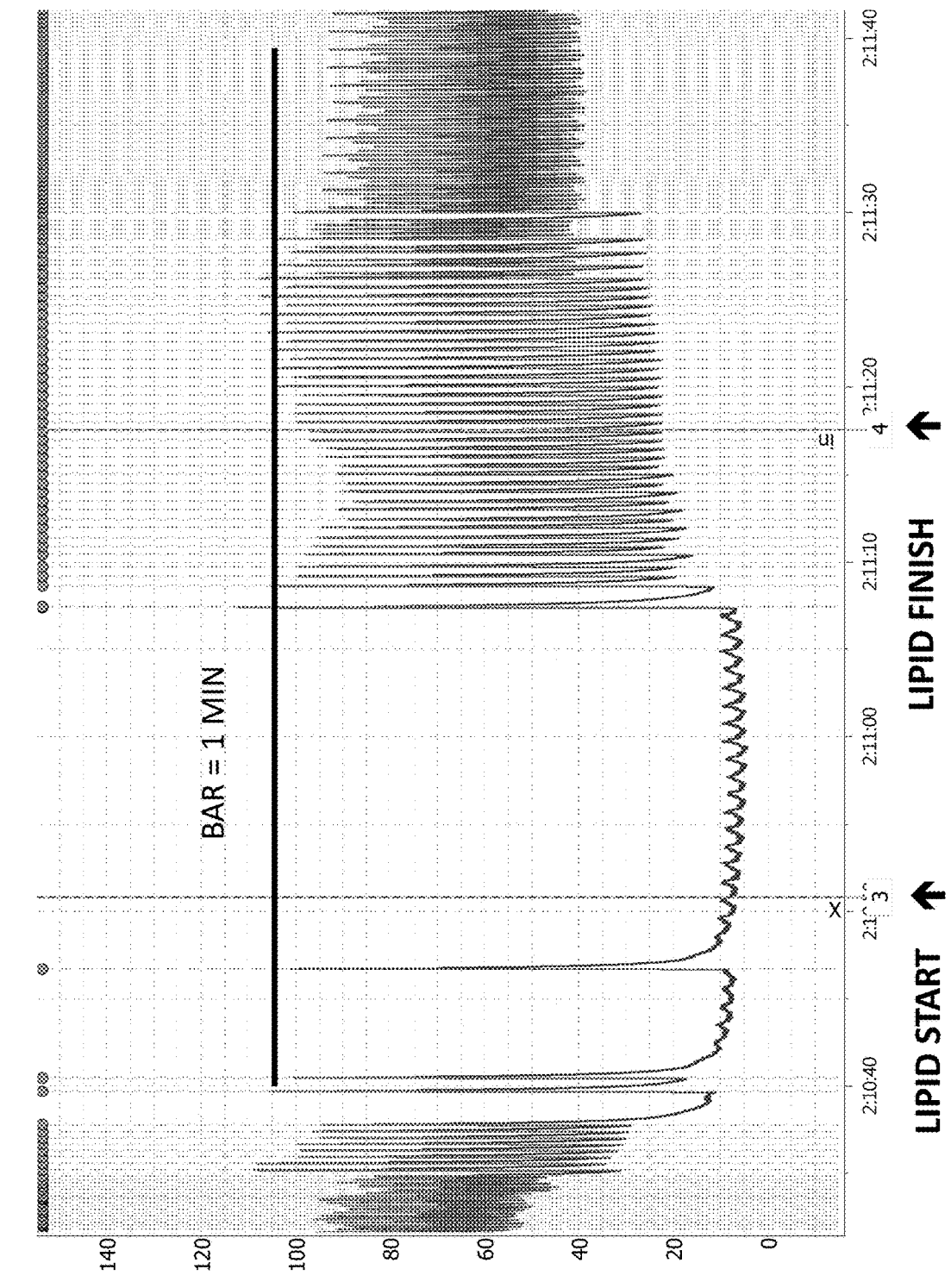
FIG. 1A – New Lipid Formulation , 40 SECOND RECOVERY

FIG. 1B   INTRALIPID 20, 3 MINUTE RECOVERY
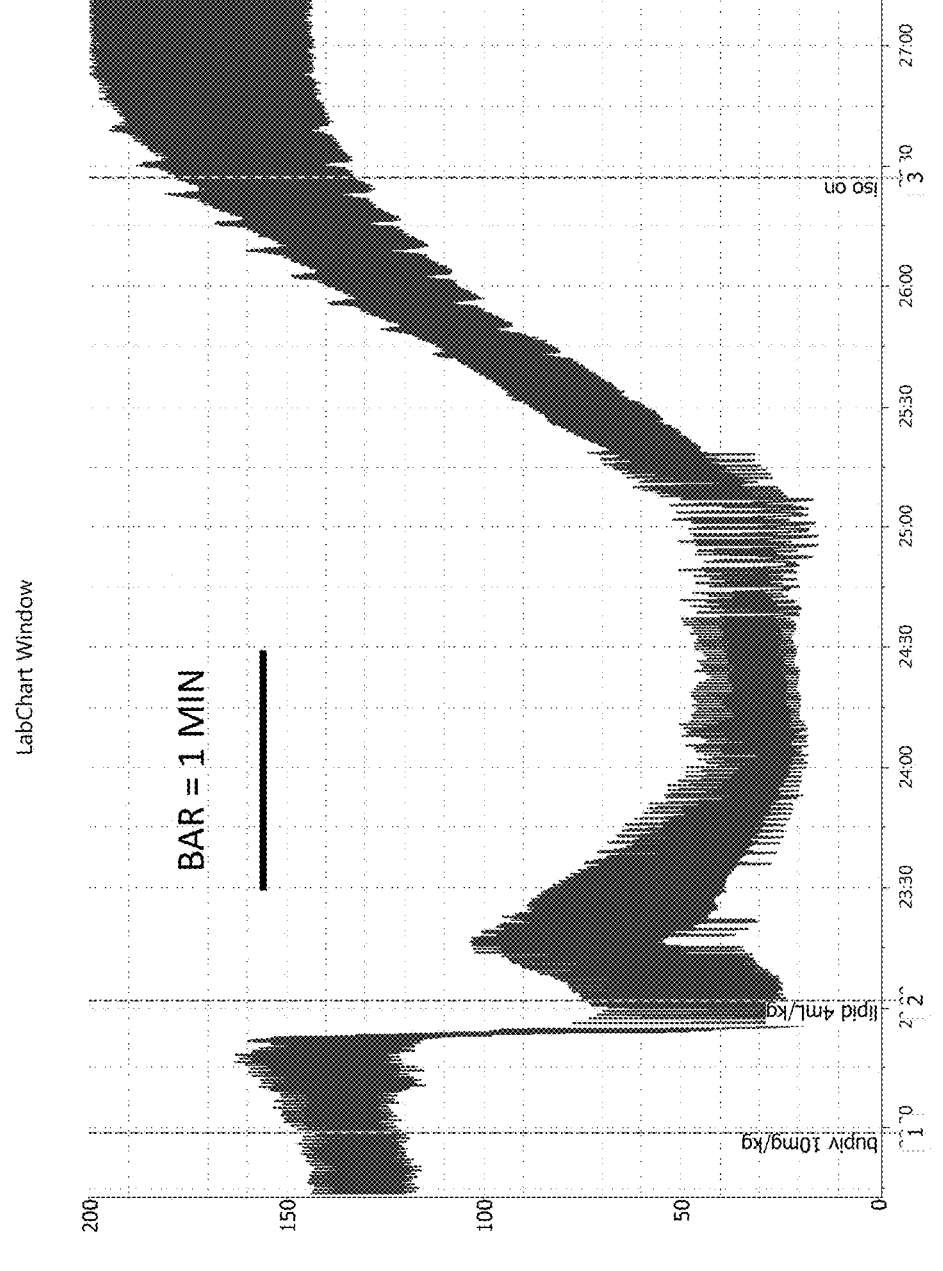
LIPID START ← ← LIPID FINISH

LIPID EMULSIONS AND USES THEREOF

CROSS-REFERENCE TO RELATED APPLICATIONS

This application is a divisional application of U.S. application Ser. No. 17/058,545, filed Nov. 24, 2020, which claims the benefit of International Patent Application number PCT/US2019/033997, filed May 24, 2019, which claims the benefit of U.S. provisional application No. 62/836,394 filed Apr. 19, 2019, U.S. provisional application No. 62/803,932 filed Feb. 11, 2019 and U.S. provisional application No. 62/676,850, filed May 25, 2018, each of which is hereby incorporated by reference in their entirety.

FIELD OF THE DISCLOSURE

The present disclosure provides lipid emulsions comprising at least 20 percent (w/v) lipid with an average particle size of about 200 to about 300 nm, and use thereof to treat subjects in need of lipid emulsion therapy.

BACKGROUND OF THE DISCLOSURE

Current evidence has illustrated that mortality is higher in post-surgical patients that experienced a hypotensive episode or an ischemia-reperfusion injury. However, data has shown that even if a hypotensive episode is treated with a compound(s) designed to increase blood pressure, the odds of surviving do not improve. This is postulated to be correlated with the organ damage caused by hypotension and/or ischemia/reperfusion. The present inventors have discovered, in part, that lipid emulsions may be successfully used to address the organ damage caused by hypotension or ischemia/reperfusion injury. Furthermore, the lipid emulsions disclosed herein have shown an increased benefit compared to other lipid emulsions for treating drug toxicity.

Intravenous lipid emulsions have been previously used experimentally. Lipid emulsions currently in use, however, suffer from several drawbacks, including the total volume needed to treat a subject, which can lead to either volume overload of the cardiovascular system or fat overload syndrome. Hence, there is a need in the art for improved lipid emulsion formulations.

SUMMARY OF THE DISCLOSURE

One aspect of the present disclosure is a lipid emulsion composition comprising at least 20 percent (w/v) lipid, about 1 to about 5 percent (w/v) emulsifier, about 1 to about 5 percent (w/v) tonicity modifier, about 58 to about 88 percent (w/v) water, and optionally an inotrope and/or other compound such as vitamin K or CoQ10 that can act as an electron acceptor and thereby improve tissue redox state, or improve mitochondrial function and metabolism including oxidative phosphorylation, wherein the particles in the lipid emulsion have an average particle diameter of about 200 nm to less than 300 nm.

Another aspect of the present disclosure is a method of treating systemic drug toxicity in a subject in need thereof. The method comprises intravenously administering to the subject a lipid emulsion composition comprising at least 20 percent (w/v) lipid, about 1 to about 5 percent (w/v) emulsifier, about 1 to about 5 percent (w/v) tonicity modifier, about 58 to about 88 percent (w/v) water, and optionally an inotrope and/or other compound such as vitamin K or CoQ10 that can act as an electron acceptor and thereby improve tissue redox state, or improve mitochondrial function and metabolism including oxidative phosphorylation, wherein the particles in the lipid emulsion have an average particle diameter of about 200 nm to less than 300 nm.

Yet another aspect of the present disclosure is a method of reducing organ injury subsequent to severe hypotension, regardless of etiology, in a subject in need thereof. The method comprises intravenously administering to the subject a lipid emulsion composition comprising at least 20 percent (w/v) lipid, about 1 to about 5 percent (w/v) emulsifier, about 1 to about 5 percent (w/v) tonicity modifier, about 58 to about 88 percent (w/v) water, and optionally an inotrope and/or other compound such as vitamin K or CoQ10 that can act as an electron acceptor and thereby improve tissue redox state, or improve mitochondrial function and metabolism including oxidative phosphorylation, wherein the particles in the lipid emulsion have an average particle diameter of about 200 nm to less than 300 nm.

A further aspect of the present disclosure is a method of treating ischemia/reperfusion injury of key organs in a subject in need thereof. The method comprises intravenously administering to the subject a lipid emulsion composition comprising at least 20 percent (w/v) lipid, about 1 to about 5 percent (w/v) emulsifier, about 1 to about 5 percent (w/v) tonicity modifier, about 58 to about 88 percent (w/v) water, and optionally an inotrope and/or other compound such as vitamin K or CoQ10 that can act as an electron acceptor and thereby improve tissue redox state, or improve mitochondrial function and metabolism including oxidative phosphorylation, wherein the particles in the lipid emulsion have an average particle diameter of about 200 nm to less than 300 nm.

An additional aspect of the present disclosure is a method of improving blood pressure in a patient with severe hypotension from any cause and reducing secondary ischemia/reperfusion injury by treating beforehand in situations where hypotension is highly likely to occur, during hypotension, or after hypotension occurs. In certain embodiments, a subject that is at risk of severe hypotension or who has suffered a severe hypotensive episode has normal cardiac function.

Another additional aspect of the present disclosure is a method of improving cardiac function, organ perfusion, or blood pressure in a patient in shock, wherein the patient has optionally been administered at least one dose of a vasopressor and/or inotrope, typically a catecholamine such as epinephrine or dopamine, the method comprising intravenously administering a lipid emulsion composition. The lipid emulsion composition may comprise at least 20 percent (w/v) lipid, about 1 to about 5 percent (w/v) emulsifier, about 1 to about 5 percent (w/v) tonicity modifier, about 58 to about 88 percent (w/v) water, and optionally an inotrope and/or other compound such as vitamin K or CoQ10 that can act as an electron acceptor and thereby improve tissue redox state, or improve mitochondrial function and metabolism including oxidative phosphorylation, wherein the particles in the lipid emulsion have an average particle diameter of about 200 nm to less than 300 nm.

A still further aspect of the present disclosure is a method of reducing the therapeutic vasopressor dose required for a patient in shock, wherein the patient has optionally been administered at least one high dose of a vasopressor, the method comprising intravenously administering a lipid emulsion composition. The lipid emulsion composition may comprise at least 20 percent (w/v) lipid, about 1 to about 5 percent (w/v) emulsifier, about 1 to about 5 percent (w/v) tonicity modifier, about 58 to about 88 percent (w/v) water, and optionally an inotrope and/or other compound such as vitamin K or CoQ10 that can act as an electron acceptor and thereby improve tissue redox state, or improve mitochondrial function and metabolism including oxidative phosphorylation, wherein the particles in the lipid emulsion have an average particle diameter of about 200 nm to less than 300 nm.

A certain aspect of the present disclosure encompasses a method of improving cardiac function, blood pressure, or organ perfusion in a patient diagnosed with end-stage or refractory heart failure, the method comprising intravenously administering a lipid emulsion. The lipid emulsion composition may comprise at least 20 percent (w/v) lipid, about 1 to about 5 percent (w/v) emulsifier, about 1 to about 5 percent (w/v) tonicity modifier, about 58 to about 88 percent (w/v) water, and optionally an inotrope and/or other compound such as vitamin K or CoQ10 that can act as an electron acceptor and thereby improve tissue redox state, or improve mitochondrial function and metabolism including oxidative phosphorylation, wherein the particles in the lipid emulsion have an average particle diameter of about 200 nm to less than 300 nm.

Another aspect of the present disclosure encompasses a method of improving cardiac function, improving blood pressure, or improving organ perfusion in a patient diagnosed with myocardial stunning, the method comprising intravenously administering a lipid emulsion. The lipid emulsion composition may comprise at least 20 percent (w/v) lipid, about 1 to about 5 percent (w/v) emulsifier, about 1 to about 5 percent (w/v) tonicity modifier, about 58 to about 88 percent (w/v) water, and optionally an inotrope and/or other compound such as vitamin K or CoQ10 that can act as an electron acceptor and thereby improve tissue redox state, or improve mitochondrial function and metabolism including oxidative phosphorylation, wherein the particles in the lipid emulsion have an average particle diameter of about 200 nm to less than 300 nm.

Other iterations, aspects, and embodiments of the present disclosure are detailed below.

BRIEF DESCRIPTION OF THE FIGURES

FIG. 1A depicts a graph showing arterial pressure versus time, and the time of administration of a local anesthetic, followed by a lipid emulsion of the present disclosure, is indicated. Of note, the arterial pressure recovers in a matter of seconds after administration of a lipid emulsion of the present disclosure.

FIG. 1B depicts a graph showing arterial pressure versus time, and the time of administration of a local anesthetic, followed by the product 20% Intralipid, is indicated. Of note, the arterial pressure recovers only after several minutes after administration of the Intralipid product.

FIGS. 2A and 2B depict a first hemorrhagic challenge with recovery, while FIGS. 2C and 2D depict the return of blood after a second hemorrhagic challenge. FIGS. 2A and 2C are from a rat pretreated with lipid. FIGS. 2B and 2D are from a rat pretreated with the same volume of saline.

DETAILED DESCRIPTION

Figure 2A:
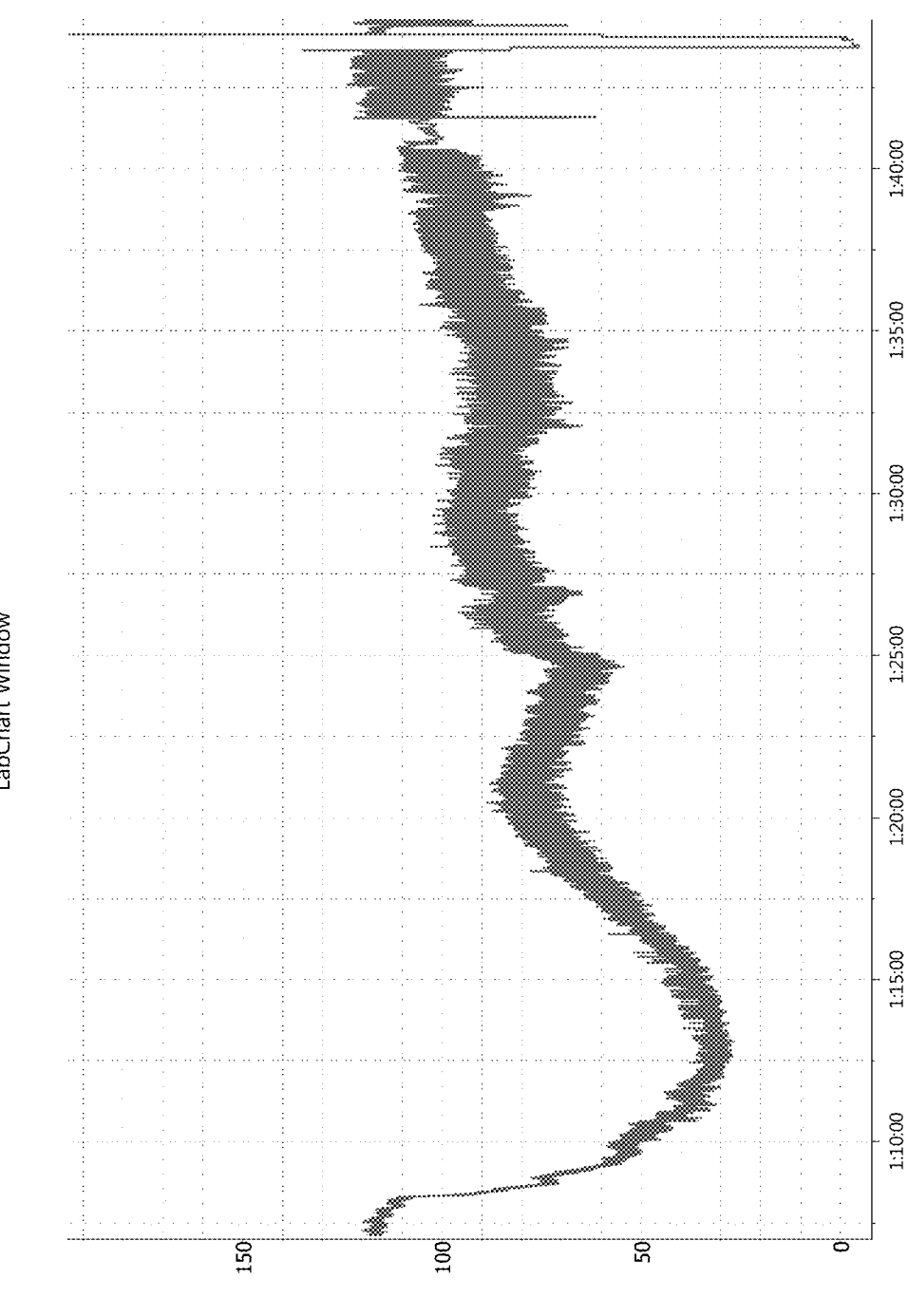
FIGS. 2A, 2B, 2C and 2D depict graphs of mean arterial pressure of approximately 30 minutes duration in a rat experiment.
Figure 2B:
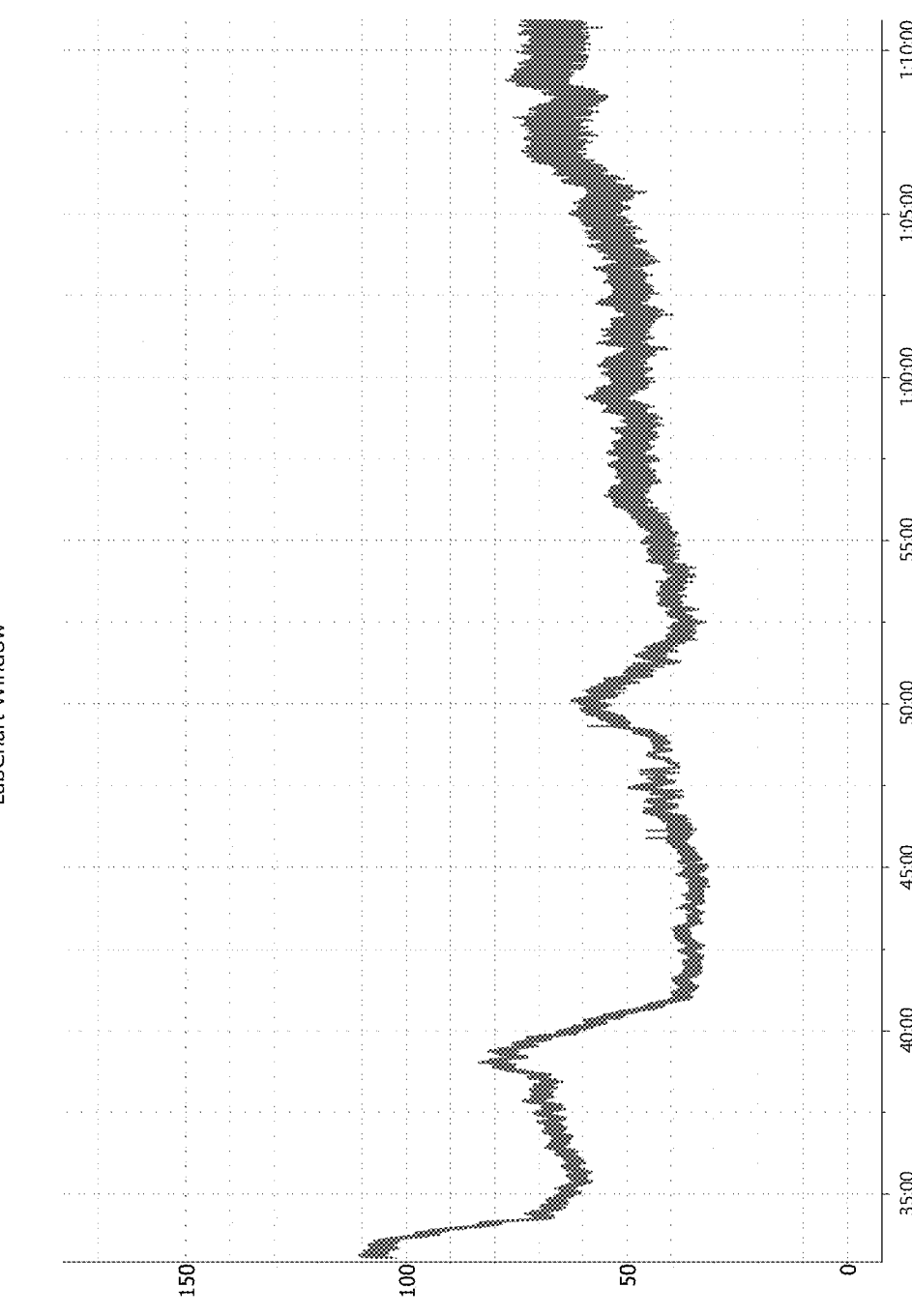

The present disclosure provides a lipid emulsion composition and methods of use thereof.

I. Lipid Emulsion Compositions

The present disclosure provides a lipid emulsion composition comprising at least 20 percent (w/v) lipid, about 1 to about 5 percent (w/v) emulsifier, about 1 to about 5 percent (w/v) tonicity modifier, about 58 to about 88 percent (w/v) water, and optionally an inotrope and/or other compound such as vitamin K or CoQ10 that can act as an electron acceptor and thereby improve tissue redox state, or improve mitochondrial function and metabolism including oxidative phosphorylation, wherein the particles in the lipid emulsion have an average particle diameter of about 200 nm to less than 300 nm.

The lipid may be a refined animal fat, a refined vegetable oil (e.g., soybean, canola, corn, sunflower, peanut, safflower, cottonseed, palm, etc.), a triglyceride, two or more triglycerides, or any combination thereof. Triglycerides may be saturated, unsaturated, or a combination thereof.

In some embodiments, the lipid is soybean oil, avocado oil, flaxseed oil, coconut oil, cottonseed oil, squalene oil, groundnut oil, olive oil, canola oil, corn oil, rapeseed oil, safflower oil, sunflower oil, an animal oil, fish oil, flavor oil, water insoluble vitamins, mineral oil, or any combination thereof. In other embodiments, the lipid is synthetic oil that has a substantially similar composition as soybean oil, avocado oil, flaxseed oil, coconut oil, cottonseed oil, squalene oil, groundnut oil, olive oil, canola oil, corn oil, rapeseed oil, safflower oil, sunflower oil, an animal oil, fish oil, mineral oil, or any combination thereof.

In some embodiments, the lipid is refined soybean oil. The major component fatty acids of soybean oil are linoleic acid (44-62% w/v), oleic acid (19-30% w/v), palmitic acid (7-14% w/v), α-linolenic acid (4-11% w/v) and stearic acid (1.4-5.5% w/v) (Padley F B: "Major Vegetable Fats," The Lipid Handbook Gunstone F D, Harwood J L, Padley F B, eds.), Chapman and Hall Ltd., Cambridge, UK (1986), pp. 88-89.) A skilled artisan will be able to use the known fatty acid profiles of commercially available animal fats or vegetable oils to substitute these fats for soybean oil. Alternatively, synthetic triglycerides may be used to produce a fat comprising about 44% to about 62% linoleic acid, about 19% to about 30% oleic acid, about 7% to about 14% palmitic acid, about 4% to about 11% α-linolenic acid, about 1.4% to about 5.5% stearic acid.

In certain embodiments, the lipid comprises about 40% to about 65% linoleic acid, about 15% to about 35% oleic acid, about 5% to about 20% palmitic acid, about 1% to about 15% α-linolenic acid, about 1% to about 10% stearic acid. In other embodiments, the lipid consists of about 40% to about 65% linoleic acid, about 15% to about 35% oleic acid, about 5% to about 20% palmitic acid, about 1% to about 15% α-linolenic acid, about 1% to about 10% stearic acid. In other embodiments, the lipid comprises about 44% to about 62% linoleic acid, about 19% to about 30% oleic acid, about 7% to about 14% palmitic acid, about 4% to about 11% α-linolenic acid, about 1.4% to about 5.5% stearic acid.

Generally speaking, a composition of the invention may comprise from about 1 to about 5% emulsifier. In some embodiments, the emulsifier may be about 1, 2, 3, 4, or 5%. In other embodiments, the emulsifier may be between about 1% and 2.5%. In certain embodiments, the emulsifier may be between about 1% and 2.2%. The emulsifier may be natural, semi-synthetic, or synthetic. In some embodiments, the emulsifier comprises lecithin, such as a synthetic lecithin. In particular embodiments, emulsifier comprises dihexanoyl-L-α-lecithin and/or one or more phospholipid. The phospholipid may be phosphatidylcholine, phosphatidylethanolamine, phosphatidylserine, phosphatidylinositol, phosphatidylglycerol, phosphatidic acid, lysophospholipids, egg phospholipid, soybean phospholipid, or any combination thereof. Common sources of industrially produced phospholipids are soya, rapeseed, sunflower, chicken eggs, bovine milk, fish eggs, etc. A preferred source is egg yolk lecithin or purified egg yolk phospholipid.

The tonicity modifier may include, for example, glycerin, sorbitol, one or more polyoxyethylated hydrocarbon, one or more $C_6$-$C_{20}$ saturated aliphatic acid, one or more $C_6$-$C_{20}$ unsaturated aliphatic acid, or any combination thereof.

A lipid emulsion composition of the present disclosure may have a pH suitable for intravenous administration, for example, between about pH 4 to about pH 10, or about pH 6 to about pH 8.9, or about pH 7 to about pH 8 or about pH 9 to about pH 10. In one embodiment, the pH may be about pH 8. In other embodiments, the pH may be between about 9.0 and 9.8, specifically between about 9.2 and about 9.6. The pH may be adjusted by adding an acid or base, as is well-known in the art.

In some embodiments, a lipid emulsion composition of the present disclosure may further comprise a biologically active compound which renders a toxic agent in a subject non-toxic or which counters the physiological effects of a toxic agent. In particular embodiments, the biologically active compound comprises an inotrope. In specific embodiments, the inotrope may comprise insulin, insulin+glucose, levosimendan, or catecholamine-type sympathomimetics like epinephrine, neosynephrine, norepinephrine, dobutamine, and dopamine. In other embodiments, a lipid emulsion composition of the present disclosure may include a compound such as vitamin K or CoQ10 that can act as an electron acceptor and thereby improve tissue redox state, or improve mitochondrial function and metabolism including oxidative phosphorylation.

A lipid emulsion composition of the present disclosure may further comprise one or more buffering agents, adsorbents, antioxidants, antimicrobial agents, vitamin K or any combination thereof. Non-limiting examples of suitable antioxidants include α-tocopherol, ascorbic acid, and deferoxamine mesylate. Antimicrobial agents may include, but are not limited to, EDTA, sodium benzoate, and benzyl alcohol. Adsorbents may include, but are not limited to, charcoal, silica gel, or mixtures thereof.

The particles in the lipid emulsion may vary in size, and are typically below about 1.0 μm, preferably about 0.5 μm or less, while having an average particle diameter of about 100 nm to less than about 300 nm, or about 250 nm to less than about 315 nm. In preferred embodiments, the size of the particle(s) is determined after terminal sterilization of the emulsion. In some embodiments, the particles in the lipid emulsion have an average particle diameter of about 210 nm to about 240 nm. In some embodiments, the particles in the lipid emulsion have an average particle diameter of about 210 nm to about 230 nm. In some embodiments, the particles in the lipid emulsion have an average particle diameter of about 220 nm to about 240 nm. In some embodiments, the particles in the lipid emulsion have an average particle diameter of about 220 nm to about 240 nm. In some embodiments, the particles in the lipid emulsion have an average particle diameter of about 230 nm to about 240 nm. In some embodiments, the particles in the lipid emulsion have an average particle diameter of about 270 to about 315, or about 280 to about 310. In certain embodiments, the particles in the lipid emulsion have an average particle diameter of about 260 to about 280 nm. In particular embodiments, the particles in the lipid emulsion have an average particle diameter of about 270 to about 290 nm. In some embodiments, the particles in the lipid emulsion have an average particle diameter of about 270 nm to about 280 nm. For instance, in some embodiments, the particles in a lipid emulsion of the present disclosure have an average particle diameter of about 220 nm, about 225 nm, about 230 nm, about 235 nm, about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, about 305 nm, or about 310 nm. Methods for measuring particle diameter are known in the art.

In preferred embodiments, the average particle diameter of a lipid emulsion of the present disclosure is about 200 nm to less than about 300 nm, which produces a safer lipid emulsion. Furthermore, in preferred embodiments where the average particle diameter of a lipid emulsion of the present disclosure is about 200 nm to less than about 300 nm, the lipid emulsion has higher effective surface area. For instance, assuming 100 mL of a lipid emulsion with an average particle size of 440 nm diameter, the total surface area is approximately 300 $m^2$. However, a lipid emulsion with an average particle size of 280 nm diameter results in a total surface area of approximately 470 $m^2$—a 56% increase. Lipid emulsions with particles greater than this range have less surface area, and are less safe, while particles below this range are too small to have the same efficacy as particles of the present disclosure. For instance, particles in this range are more effective, which means a lower volume of particles needs to be administered, which is safer for the patient. By way of example, administering less means that lipid compositions of the present invention are less likely to occlude blood vessels or result in volume overload or fat overload syndrome.

In certain embodiments, at least 50% of the particles have a particle diameter less than 300 nm. For example, about 50%, about 55%, about 60%, about 65%, about 70%, about 75%, about 80%, about 85%, or about 90% of the particles have a particle diameter less than 300 nm. In each of these embodiments, the particle size standard deviation is 150 nm or less, 100 nm or less, 75 nm or less, 50 nm or less, 25 nm or less, or 10 nm or less.

In certain embodiments, at least 50% of the particles have a particle diameter less than 290 nm. For example, about 50%, about 55%, about 60%, about 65%, about 70%, about 75%, about 80%, about 85%, or about 90% of the particles have a particle diameter less than 290 nm. In each of these embodiments, the particle size standard deviation is 150 nm or less, 100 nm or less, 75 nm or less, 50 nm or less, 25 nm or less, or 10 nm or less.

In certain embodiments, at least 50% of the particles have a particle diameter less than 280 nm. For example, about 50%, about 55%, about 60%, about 65%, about 70%, about 75%, about 80%, about 85%, or about 90% of the particles have a particle diameter less than 280 nm. In each of these embodiments, the particle size standard deviation is 150 nm or less, 100 nm or less, 75 nm or less, 50 nm or less, 25 nm or less, or 10 nm or less.

In certain embodiments, at least 50% of the particles have a particle diameter less than 270 nm. For example, about 50%, about 55%, about 60%, about 65%, about 70%, about 75%, about 80%, about 85%, or about 90% of the particles have a particle diameter less than 270 nm. In each of these embodiments, the particle size standard deviation is 150 nm or less, 100 nm or less, 75 nm or less, 50 nm or less, 25 nm or less, or 10 nm or less.

In certain embodiments, at least 50% of the particles have a particle diameter less than 260 nm. For example, about 50%, about 55%, about 60%, about 65%, about 70%, about 75%, about 80%, about 85%, or about 90% of the particles have a particle diameter less than 260 nm. In each of these embodiments, the particle size standard deviation is 150 nm or less, 100 nm or less, 75 nm or less, 50 nm or less, 25 nm or less, or 10 nm or less.

In certain embodiments, at least 50% of the particles have a particle diameter less than 250 nm. For example, about 50%, about 55%, about 60%, about 65%, about 70%, about 75%, about 80%, about 85%, or about 90% of the particles have a particle diameter less than 250 nm. In each of these embodiments, the particle size standard deviation is 150 nm or less, 100 nm or less, 75 nm or less, 50 nm or less, 25 nm or less, or 10 nm or less.

In certain embodiments, at least 50% of the particles have a particle diameter of about 240 nm or less. For example, about 50%, about 55%, about 60%, about 65%, about 70%, about 75%, about 80%, about 85%, or about 90% of the particles have a particle diameter of about 240 nm or less. In each of these embodiments, the particle size standard deviation is 150 nm or less, 100 nm or less, 75 nm or less, 50 nm or less, 25 nm or less, or 10 nm or less.

In certain embodiments, at least 50% of the particles have a particle diameter of about 230 nm or less. For example, about 50%, about 55%, about 60%, about 65%, about 70%, about 75%, about 80%, about 85%, or about 90% of the particles have a particle diameter of about 230 nm or less. In each of these embodiments, the particle size standard deviation is 150 nm or less, 100 nm or less, 75 nm or less, 50 nm or less, 25 nm or less, or 10 nm or less.

In certain embodiments, at least 80% of the particles have a particle diameter less than 250 nm, and at least 50% of the particle have a diameter of about 240 nm or less. For example, about 50%, about 55%, about 60%, about 65%, about 70%, about 75%, about 80%, about 85%, or about 90% of the particles have a particle diameter of about 240 nm or less. In each of these embodiments, the particle size standard deviation is 150 nm or less, 100 nm or less, 75 nm or less, 50 nm or less, 25 nm or less, or 10 nm or less.

In certain embodiments, at least 90% of the particles have a particle diameter less than 250 nm, and at least 50% of the particle have a diameter of about 240 nm or less. For example, about 50%, about 55%, about 60%, about 65%, about 70%, about 75%, about 80%, about 85%, or about 90% of the particles have a particle diameter of about 240 nm or less. In each of these embodiments, the particle size standard deviation is 150 nm or less, 100 nm or less, 75 nm or less, 50 nm or less, 25 nm or less, or 10 nm or less.

In certain embodiments, at least 80% of the particles have a particle diameter less than 250 nm, and at least 50% of the particle have a diameter of about 230 nm or less. For example, about 50%, about 55%, about 60%, about 65%, about 70%, about 75%, about 80%, about 85%, or about 90% of the particles have a particle diameter of about 250 nm or less. In each of these embodiments, the particle size standard deviation is 150 nm or less, 100 nm or less, 75 nm or less, 50 nm or less, 25 nm or less, or 10 nm or less.

In certain embodiments, at least 90% of the particles have a particle diameter less than 250 nm, and at least 50% of the particles have a diameter of about 230 nm or less. For example, about 50%, about 55%, about 60%, about 65%, about 70%, about 75%, about 80%, about 85%, or about 90% of the particles have a particle diameter of about 250 nm or less. In each of these embodiments, the particle size standard deviation is 150 nm or less, 100 nm or less, 75 nm or less, 50 nm or less, 25 nm or less, or 10 nm or less.

In certain embodiments, at least 80% of the particles have a particle diameter less than 300 nm, and at least 50% of the particles have a diameter of about 290 nm or less. For example, about 50%, about 55%, about 60%, about 65%, about 70%, about 75%, about 80%, about 85%, or about 90% of the particles have a particle diameter of about 300 nm or less. In each of these embodiments, the particle size standard deviation is 150 nm or less, 100 nm or less, 75 nm or less, 50 nm or less, 25 nm or less, or 10 nm or less.

In certain embodiments, at least 90% of the particles have a particle diameter less than 300 nm, and at least 50% of the particles have a diameter of about 280 nm or less. For example, about 50%, about 55%, about 60%, about 65%, about 70%, about 75%, about 80%, about 85%, or about 90% of the particles have a particle diameter of about 300 nm or less. In each of these embodiments, the particle size standard deviation is 150 nm or less, 100 nm or less, 75 nm or less, 50 nm or less, 25 nm or less, or 10 nm or less.

In certain embodiments, at least 80% of the particles have a particle diameter less than 290 nm, and at least 50% of the particles have a diameter of about 280 nm or less. For example, about 50%, about 55%, about 60%, about 65%, about 70%, about 75%, about 80%, about 85%, or about 90% of the particles have a particle diameter of about 290 nm or less. In each of these embodiments, the particle size standard deviation is 150 nm or less, 100 nm or less, 75 nm or less, 50 nm or less, 25 nm or less, or 10 nm or less.

In certain embodiments, at least 90% of the particles have a particle diameter less than 290 nm, and at least 50% of the particles have a diameter of about 280 nm or less. For example, about 50%, about 55%, about 60%, about 65%, about 70%, about 75%, about 80%, about 85%, or about 90% of the particles have a particle diameter of about 290 nm or less. In each of these embodiments, the particle size standard deviation is 150 nm or less, 100 nm or less, 75 nm or less, 50 nm or less, 25 nm or less, or 10 nm or less.

In certain embodiments, at least 80% of the particles have a particle diameter less than 280 nm, and at least 50% of the particles have a diameter of about 275 nm or less. For example, about 50%, about 55%, about 60%, about 65%, about 70%, about 75%, about 80%, about 85%, or about 90% of the particles have a particle diameter of about 280 nm or less. In each of these embodiments, the particle size standard deviation is 150 nm or less, 100 nm or less, 75 nm or less, 50 nm or less, 25 nm or less, or 10 nm or less.

In certain embodiments, at least 90% of the particles have a particle diameter less than 280 nm, and at least 50% of the particles have a diameter of about 275 nm or less. For example, about 50%, about 55%, about 60%, about 65%, about 70%, about 75%, about 80%, about 85%, or about 90% of the particles have a particle diameter of about 280 nm or less. In each of these embodiments, the particle size standard deviation is 150 nm or less, 100 nm or less, 75 nm or less, 50 nm or less, 25 nm or less, or 10 nm or less.

Methods for making lipid emulsions and controlling the particle size of lipid emulsions are known in the art and include but are not limited to, filtration. See, for example, *AAPS PharmSciTech* 2010, 11(4): 1526-1540, which is hereby incorporated by reference in its entirety. Through additional filtration and/or by modifying the processing technique, compositions of the present disclosure with increased lipid concentrations but smaller particles sizes and narrower particle size distributions are obtained.

Lipid emulsion compositions of the present disclosure are stable. In some embodiments, the average particle diameter of the composition changes by 30% or less following storage at between 15° C. to 30° C. for 7 days. In some embodiments, the average particle diameter of the composition changes by 30% or less following storage between 15° C. to 30° C. for 14 days. In some embodiments, the average particle diameter of the composition changes by 30% or less following storage between 15° C. to 30° C. for 3 months. In some embodiments, the average particle diameter of the composition changes by 30% or less following storage between 15° C. to 30° C. for 6 months. In some embodiments, the average particle diameter of the composition changes by 30% or less following storage between 15° C. to 30° C. for 12 months. In some embodiments, the average particle diameter of the composition changes by 30% or less following storage between 15° C. to 30° C. for 24 months. In each of the above embodiments, the average particle diameter of the composition may changes by 30%, 25%, 20%, 15%, 10%, 5%, or less.

In some embodiments, the average particle diameter of the composition changes by 30% or less following storage at 25° C. for 7 days. In some embodiments, the average particle diameter of the composition changes by 30% or less following storage at 25° C. for 14 days. In some embodiments, the average particle diameter of the composition changes by 30% or less following storage at 25° C. for 3 months. In some embodiments, the average particle diameter of the composition changes by 30% or less following storage at 25° C. for 6 months. In some embodiments, the average particle diameter of the composition changes by 30% or less following storage at 25° C. for 12 months. In some embodiments, the average particle diameter of the composition changes by 30% or less following storage at 25° C. for 24 months. In each of the above embodiments, the average particle diameter of the composition may changes by 30%, 25%, 20%, 15%, 10%, 5%, or less.

In some embodiments, a lipid emulsion of the present disclosure may be stored in pre-filled syringes, vials, or bags.

II. Methods of Use

Lipid emulsion compositions of the present disclosure are more efficacious than prior art lipid emulsions, and can be administered in reduced volumes contributing to greater patient safety and comfort during administration. For instance, the reduced particle size of the present disclosure is postulated to reduce the likelihood of occluding pulmonary capillaries. Moreover, the reduced volume proportionately reduces the likelihood of complications related to the volume of lipid emulsion infused, namely, cardiovascular volume overload, pulmonary edema and/or fat overload syndrome. Accordingly, the present disclosure also provides methods of using lipid emulsion compositions of the present disclosure. Generally speaking, the method comprises intravenously administering to a subject in need thereof a lipid emulsion composition of the present disclosure. A "subject in need thereof" is known in the art, and may include the subjects (and uses) disclosed in U.S. Pat. Nos. 7,261,903, 8,834,919, U.S. Ser. No. 15/775,452, and PCT Application No. PCT/US2018/012623, each of which is hereby incorporated by reference in its entirety.

Lipid emulsions of the present disclosure may be used to prevent or treat organ injury (e.g. heart, kidney, or brain injury) caused by severe hypotension, by organ reperfusion that occurs after resolution of the hypotension, or other ischemia/reperfusion injury. Stated another way, a lipid composition of the present disclosure may be administered to a subject to prevent subsequent organ injury after a severe hypotensive episode. A non-limiting example of such an episode is severe hypotension during surgery. Notably, interventions (such as alarms) to warn of dangerous hypotensive episodes have not improved patient outcomes. One possible explanation for this is the fact that simply treating the hypotensive episode (e.g. bringing blood pressure back up) doesn't address the organ injury caused by the hypotensive episode.

(a) Dosing and Administration

As used herein, the term "therapeutically effective amount" means an amount of a substance (e.g., a lipid emulsion) that leads to measurable and beneficial effects for the subject administered the substance, i.e., significant efficacy. A therapeutically effective amount of a lipid emulsion, i.e. a dose, may be administered to the subject as a bolus or as repeated boluses, as an infusion, or as a combination of a bolus or loading dose followed by an infusion. When administered as a bolus, a dose may be administered all at once, or the dose may be divided into smaller doses (e.g., 1, 2, 3, or more) and administered at regular intervals (e.g., minutes or hours) or over a given timeframe (e.g., the remainder of the intraoperative period). When administered as an infusion, the infusion can occur at a single rate or the rate can vary. A single dose or multiple doses may be administered.

Typically speaking, a composition of the invention is administered intravenously. In certain embodiments, however, a composition of the invention may be administered via intraosseous injection. This is particularly applicable to patients that may not have venous access (e.g. a child or person down in the field).

A therapeutically effective amount, or dose, of a lipid emulsion administered according to this disclosure can be determined using standard clinical techniques and may be influenced by the circumstances surrounding the case, including the amount of the fat in the emulsion and its composition, the condition of the patient, and the intended use, among other considerations. For example, in embodiments where the lipid emulsion comprises 20% lipid, a suitable dose will typically be less than about 250 mL. In some examples, a suitable dose may be about 1 mL to about 250 mL, about 10 mL to about 250 mL, about 50 mL to about 250 mL, or about 100 mL to about 250 mL. In some examples, a suitable dose may be about 10 mL to about 100 mL. In other examples, a suitable dose may be about 10 mL to about 50 mL or about 50 mL to about 100 mL. In other examples, a suitable dose may be about 100 mL to about 150 mL or about 150 mL to about 200 mL. In other examples, a suitable dose may be about 10 mL to about 35 mL, about 25 mL to about 50 mL, about 35 mL to about 60 mL, about 50 mL to about 75 mL, about 60 mL to about 85 mL, about 75 mL to about 100 mL, about 85 mL to about 110 mL, about 100 mL to about 125 mL, about 110 mL to about 135 mL, or about 125 mL to about 150 mL. In other examples, a suitable dose may be about 10 mL, about 15 mL, about 20 m L, about 25 mL, about 30 mL, about 35 mL, about 40 mL, about 45 mL, about 50 mL, about 55 mL, about 60 mL, about 65 mL, about 70 mL, about 75 mL, about 80 mL, about 85 mL, about 90 mL, about 95 mL, about 100 mL, about 105 mL, about 110 mL, about 115 mL, about 120 mL, or about 125 mL. Based on these disclosures for a 20% lipid emulsion, a skilled artisan will be able to determine suitable doses for other lipid emulsions described herein.

In some embodiments, a suitable dose may be about 1 ml/kg body weight to about 15 mk/kg bodyweight. For instance, a suitable dose may be about 1, 2, 3, 4, 5, 6, 7, 8, 9, 10, 11, 12, 13, 14, or 15 ml/kg body weight.

A subject of this disclosure is a human or animal that experiences a severe hypotensive episode. In some embodiments, a subject is receiving perioperative care. Suitable subjects may include a human, a livestock animal, a companion animal, a laboratory animal, or a zoological animal.

In a preferred embodiment, a subject is human. Also contemplated are subjects that have an increased risk of injury following intraoperative hypotension, including, but not limited to, subjects with hypotension during general anesthesia with inhaled (volatile) anesthetics or after induction of a general anesthesia with intravenous agents such as propofol; vasoplegia, cardiovascular disease, coronary artery disease, or diabetes; subjects taking medications {e.g. angiotensin converting enzyme inhibitors, angiotensin receptor blockers, etc.); surgical bleeding, and subjects with drugs in their bloodstream that cause hemodynamic instability {e.g. cocaine).

Severe hypotensive episodes may occur during surgery. In one aspect, administration of a lipid composition, as described herein, to a subject may occur before a surgical procedure begins, with the first incision marking the start of surgery. For example, administration may occur about one minute before a surgical procedure, about five minutes before a surgical procedure, about ten minutes before a surgical procedure, about thirty minutes before a surgical procedure or more. In another example, administration may occur about one hour, about two hours, or about four hours before a surgical procedure. In still another example, administration may occur about six hours, about twelve hours, about eighteen hours or about twenty-four hours before a surgical procedure. Administration before surgery may be desirable for all subjects, or only for subjects at greater risk for intraoperative hypotension.

In another aspect, administration to a subject may occur intraoperatively, following intraoperative hypotension and after the subject's mean arterial pressure (MAP) is greater than or equal to 66 mgHg, preferably for at least about one minute.

In yet another aspect, administration to a subject may occur postoperatively following intraoperative hypotension, provided the subject's MAP is greater than or equal to 66 mgHg. In another aspect, administration may occur as any combination of before surgery; intraoperatively following intraoperative hypotension and after the subject's MAP is greater than or equal to 66 mgHg; and postoperatively following intraoperative hypotension, provided the subject's MAP is greater than or equal to 66 mgHg.

(b) Intraoperative Hypotension

The present disclosure provides methods for decreasing cellular and organ injury associated with intraoperative hypotension by intravenously administering to a subject a therapeutically effective amount of a lipid emulsion, following a period of intraoperative hypotension and after the subject's mean arterial blood pressure has recovered. Non-limiting examples of injuries contemplated herein include myocardial injury, myocardial infarction, and acute kidney injury. Also disclosed herein are methods for preventing injuries associated with intraoperative hypotension prior to the start of surgery, particularly for subjects that have an increased risk for intraoperative hypotension.

As used herein, the term "perioperative" describes the time period describing the duration of a subject's surgical procedure commencing after admission. The perioperative period consists of a preoperative period, an intraoperative period, and a postoperative period. As used herein, the term "intraoperative" refers to a period during a surgical procedure that begins when a subject is transferred to an operating room table and ends with the transfer of the subject to a post-anesthesia care unit or intensive care unit. A "postoperative period" begins with the transfer of a subject from an operating room table to a recovery unit. As such, the postoperative period immediately follows the intraoperative period. In some embodiments, general anesthesia is used during the intraoperative period. In other embodiments, regional anesthesia is used during the intraoperative period. For example, a peripheral nerve block, a spinal block, or an epidural may be used during the intraoperative period. A sedative may optionally be used with regional anesthesia. During minimal sedation, a subject feels relaxed, can understand and answer questions, and is able to follow instructions. During moderate sedation, a subject feels drowsy and may sleep through much of the procedure, but typically is easily awakened when spoken to. During deep sedation, a subject sleeps through the procedure with little or no memory of the procedure room, breathing may slow, and the subject might sleep until the medication(s) wear off.

The term "severe hypotension," as used herein, refers to a mean arterial pressure (MAP) measurement that is below 66 mgHg. Organ injury associated with severe hypotension typically becomes more common as MAP decreases and/or with prolonged hypotension.

The term "intraoperative hypotension," as used herein, refers to a mean arterial pressure (MAP) measurement that is below 66 mgHg during an intraoperative period. Intraoperative hypotension may occur for at least about 30 seconds, at least about 1 minute, at least about 5 minutes, at least about 10 minutes, at least about 13 minutes, at least about 15 minutes, or more. In some aspects, intraoperative hypotension may occur for about 30 seconds to about 60 seconds. In other aspects, intraoperative hypotension may occur for about 1 minute to about 30 minutes. In other aspects, intraoperative hypotension may occur for about 1 minute to about 10 minutes, or about 1 minute to about 5 minutes. In other aspects, intraoperative hypotension may occur for about 5 minutes to about 15 minutes, or about 5 minutes to about 10 minutes. In other aspects, intraoperative hypotension may occur for about 10 minutes to about 30 minutes, or about 10 minute to about 20 minutes. In other aspects, intraoperative hypotension may occur for less than about 1 minute, less than about 5 minutes, less than about 10 minutes, less than about 13 minutes, less than about 15 minutes, less than about 20 minutes, less than about 25 minutes, or less than about 30 minutes. A subject's MAP is said to have recovered when MAP is greater than or equal to 66 mgHg. A subject's MAP can recover as result of an intervention (e.g. reperfusion therapy, etc.) or without an intervention. Methods for measuring MAP are well-known in the art.

The term "shock" refers to a state of generalized hypoperfusion where blood flow to vital organs and tissues is decreased. In one aspect, intraoperative hypotension can occur without shock. As a non-limiting example, brief and/or mild intraoperative hypotension does not imply shock. Conversely, in another aspect, shock can occur without hypotension. For example, in a setting of intense, systemic vasoconstriction, blood vessels are constricted so that perfusion (blood flow) to organs is limited despite a normal blood pressure. In still another aspect, intraoperative hypotension can occur with shock (e.g. before, after, or concurrently). For example, intraoperative hypotension can occur during pathological conditions that cause shock state, e.g., hemorrhage, anaphylaxis, cardiogenic, etc.

A "reperfusion therapy" is a medical treatment to restore blood flow, either through or around, a blockage. Reperfusion therapy may include pharmacologic reperfusion, volume infusion, surgery, percutaneous transluminal coronary angioplasty/stenting (PCTA), or other therapies. Non-limiting classes of drugs used in reperfusion therapy may include thrombolytics and fibrinolytics {e.g., streptokinase, alteplase, reteplase, tenecteplase, inotropes or vasopressors to increase blood pressure and/or perfusion of vital organs, etc.). Non-limiting examples of products used for volume infusion include blood products and crystalloid or colloid solutions. Surgeries performed may be minimally-invasive endovascular procedures {e.g., coronary angioplasty, stents, etc.) or more invasive {e.g. coronary artery bypass grafting, etc.). In some instances, a subject's MAP can recover following reperfusion therapy. The terms "reperfusion therapy" and "reperfusion intervention" may be used interchangeably.

In some aspects, intraoperative hypotension can occur during non-cardiac surgery. In these instances, a subject's blood flow to an organ can be reduced but not completely stopped during the period of intraoperative hypotension. Non-limiting causes for the ischemia include bleeding, general anesthesia, regional anesthesia {e.g., sympathectomy caused by neuraxial anesthesia, etc.), other drugs administered during surgery {e.g. sedatives, etc.), or a combination thereof. Alternatively, a subject's blood flow can be completely stopped during the period of intraoperative hypotension. In other aspects, the intraoperative hypotension can occur during cardiac surgery. In these instances, a subject's blood flow to the heart is often completely stopped at times. When blood flow is restarted or normalized in each of these situations, the subsequent organ damage can be reduced by treatment with a lipid emulsion described herein.

In each of the above embodiments and aspects, intraoperative hypotension may be treated by administering a lipid emulsion composition of the present disclosure.
(c) Myocardial Injury, Acute Kidney Injury, and Brain Injury Myocardial injury, acute kidney injury, and brain injury are three examples of organ injuries associated with severe hypotension, and the present disclosure provides methods for preventing and/or decreasing myocardial injury and/or acute kidney injury and/or brain injury in a subject. As used herein, the term "preventing" refers to both complete prevention (i.e. no injury occurs) or a decrease in injury as compared to a control group that did not receive the lipid emulsion (i.e. prevention of some amount of injury).

In one aspect, the present disclosure provides methods for preventing myocardial injury, acute kidney injury, or brain injury in a subject. The method comprises intravenously administering to a subject, before a severe hypotensive episode, a therapeutically effective amount of a lipid emulsion. In some embodiments, a lipid emulsion may be administered to a subject during perioperative care (e.g. before surgery). Suitable lipid emulsions are detailed above in Section I, and details of their administration are described above.

Suitable subjects may have a mean arterial pressure (MAP) greater than or equal to 66 mgHg at the time of administration. In certain embodiments, the subject has a greater risk for severe hypotension. Non-limiting examples of subjects at greater risk for severe hypotension include subjects under general or regional anesthesia that also have: a prior history of intraoperative hypotension, have vasoplegia, have cardiovascular disease, have coronary artery disease, have diabetes, are taking angiotensin converting enzyme inhibitors, are taking angiotensin receptor blockers, and/or have drugs in their bloodstream that cause hemodynamic instability including but not limited to cocaine.

In another aspect, the present disclosure provides methods for decreasing myocardial injury, acute kidney injury, or a brain injury in a subject following a severe hypotensive episode, wherein the severe hypotension occurred with or without shock. In some aspects, the severe hypotension occurred during non-cardiac surgery and the subject's blood flow was reduced but not completely occluded during the period of severe hypotension. In other aspects, the severe hypotension occurred during non-cardiac surgery and the subject's blood flow was completely occluded during the period of severe hypotension. In still other aspects, the severe hypotension occurred during cardiac surgery. In aspects involving non-cardiac surgery, the subject may be under general anesthesia or regional anesthesia during the surgical procedure. In aspects involving cardiac surgery, the subject is under general anesthesia during the surgical procedure. The method comprises intravenously administering to the subject a therapeutically effective amount of a lipid emulsion just as or soon after the subject's mean arterial pressure (MAP) is recovered to greater than or equal to 66 mgHg. For instance, the lipid emulsion may be administered at 10, 20, 30, 40, 50 or 60 seconds after the subject's MAP recovers to greater than or equal to 66 mgHg. In some embodiments, the lipid emulsion may be administered at 1, 2, 3, 4, 5, 6, 7, 8, 9, or 10 minutes after the subject's MAP recovers to greater than or equal to 66 mgHg. The lipid emulsion can be administered intraoperatively or postoperatively, preferably during the intraoperative period but after the subject's MAP recovered.

In another aspect, the present disclosure provides methods for preventing or decreasing myocardial injury, acute kidney injury, or brain injury in a subject following general and/or regional anesthesia. The method comprises intravenously administering to a subject, before surgery begins, a therapeutically effective amount of a lipid emulsion of the present invention. Suitable subjects have a mean arterial pressure (MAP) greater than or equal to 66 mgHg, and are further described above in Section (a). In certain embodiments, the subject has a greater risk for intraoperative hypotension.
(d) Myocardial Infarction The present disclosure also provides methods for preventing and/or decreasing postoperative myocardial infarction. The term "decreasing postoperative myocardial infarction" refers to decreasing a relative risk of myocardial infarction and/or decreasing a number of myocardial infarctions.

In one aspect, the present disclosure provides methods for preventing postoperative myocardial infarction in a subject. The method comprises intravenously administering to a subject, before surgery begins, a therapeutically effective amount of a lipid emulsion of the present disclosure.

In another aspect, the present disclosure provides methods for decreasing or preventing postoperative myocardial infarction in a subject following intraoperative hypotension. In further aspects, the intraoperative hypotension occurred during non-cardiac surgery and the subject's blood flow was reduced but not completely stopped during the period of intraoperative hypotension. In other aspects, the intraoperative hypotension occurred during non-cardiac surgery and the subject's blood flow was completely occluded during the period of intraoperative hypotension. In still other aspects, the intraoperative hypotension occurred during cardiac surgery. In aspects involving non-cardiac surgery, the subject may be under general anesthesia or regional anesthesia during the surgical procedure. In aspects involving cardiac surgery, the subject is under general anesthesia during the surgical procedure. The method comprises intravenously administering to the subject a therapeutically effective amount of a lipid emulsion after the subject's mean arterial pressure (MAP) is recovered to greater than or equal to 66 mgHg. The lipid emulsion can be administered intraoperatively or postoperatively, preferably during the intraoperative period but after the subject's MAP recovered.

In another aspect, the present disclosure provides methods for decreasing postoperative myocardial infarction following general anesthesia. The method comprises intravenously administering to a subject that is not in shock, and/or was not in shock, a therapeutically effective amount of a lipid emulsion after the subject has received one or more reperfusion therapies to restore the subject's mean arterial pressure (MAP) to 66 mgHg or greater. The lipid emulsion can be administered intraoperatively or postoperatively, preferably during the intraoperative period but after the subject's MAP recovered.

In each of the above aspects, a decrease in postoperative myocardial infarction may be seen at one or more times prior to discharge {e.g., about 2 hours postoperatively to discharge), at one or more times following discharge (e.g., discharge to about 12 months postoperatively), or a combination thereof. Timing may be expressed relative to when the lipid emulsion was first administered ("about X amount of time after administration"), relative to the start of postoperative period ("about X amount of time postoperatively"), or relative to the start of some other clinical milestone (e.g. discharge, etc.). A skilled artisan using a milestone not expressly stated will be able to adjust the timing according to the disclosures herein.

(e) Postoperative Mortality

The present disclosure also provides methods for decreasing postoperative mortality. A "decrease in postoperative mortality" refers to a decrease in the relative risk of dying up to a year after surgery. In one aspect, the method comprises intravenously administering to a subject, before a surgical procedure begins, a therapeutically effective amount of a lipid emulsion of the present disclosure.

In another aspect, the disclosure provides methods for decreasing postoperative mortality in a subject following intraoperative hypotension. The method comprises intravenously administering to the subject a therapeutically effective amount of a lipid emulsion after the subject's mean arterial pressure (MAP) is recovered to greater than or equal to 66 mgHg. A lipid emulsion of the present disclosure can be administered intraoperatively or postoperatively, preferably during the intraoperative period but after the subject's MAP recovered.

A decrease in postoperative mortality may be seen at one or more times prior to discharge (e.g., about 24 hours postoperatively to discharge), at one or more times following discharge (e.g., discharge to about 12 months postoperatively), or a combination thereof. For example, in some embodiments, 24-hour postoperative mortality is decreased by at least 10% as compared to a control group that did not receive the lipid emulsion. 24-hour postoperative mortality may be decreased by about 10%, about 20%, about 30%, about 40%, or about 50%. In another example, 24-hour postoperative mortality may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In other embodiments, 7-day postoperative mortality is decreased by at least 10% as compared to a control group that did not receive the lipid emulsion. For example, 7-day postoperative mortality may be decreased by about 10%, about 20%, about 30%, about 40%, or about 50%. In another example, 7-day postoperative mortality may be decreased by about 60%, about 70%, about 80%, about 90%, or about 100%. In still another example, 7-day postoperative mortality may be decreased by about 2-fold, about 3-fold, about 4-fold, about 5-fold, about 10-fold, or more.

In further embodiments, 30-day postoperative mortality is decreased by at least 10% as compared to a control group that did not receive the lipid emulsion. For example, 30-day postoperative mortality may be decreased by about 10%, about 20%, about 30%, about 40%, or about 50%. In another example, 30-day postoperative mortality may be decreased by about 60%, about 70%, about 80%, about 90%, or about 100%. In still another example, 30-day postoperative mortality may be decreased by about 2-fold, about 3-fold, about 4-fold, about 5-fold, about 10-fold, or more.

In still other embodiments, 3-month postoperative mortality is decreased by at least 10% as compared to a control group that did not receive the lipid emulsion. For example, 3-month postoperative mortality may be decreased by about 10%, about 20%, about 30%, about 40%, or about 50%. In another example, 3-month postoperative mortality may be decreased by about 60%, about 70%, about 80%, about 90%, or about 100%. In still another example, 3-month postoperative mortality may be decreased by about 2-fold, about 3-fold, about 4-fold, about 5-fold, about 10-fold, or more.

In still other embodiments, 6-month postoperative mortality is decreased by at least 10% as compared to a control group that did not receive the lipid emulsion. For example, 6-month postoperative mortality may be decreased by about 10%, about 20%, about 30%, about 40%, or about 50%. In another example, 6-month postoperative mortality may be decreased by about 60%, about 70%, about 80%, about 90%, or about 100%. In still another example, 6-month postoperative mortality may be decreased by about 2-fold, about 3-fold, about 4-fold, about 5-fold, about 10-fold, or more.

In still other embodiments, 12-month postoperative mortality is decreased by at least 10% as compared to a control group that did not receive the lipid emulsion. For example, 12-month postoperative mortality may be decreased by about 10%, about 20%, about 30%, about 40%, or about 50%. In another example, 12-month postoperative mortality may be decreased by about 60%, about 70%, about 80%, about 90%, or about 100%. In still another example, 12-month postoperative mortality may be decreased by about 2-fold, about 3-fold, about 4-fold, about 5-fold, about 10-fold, or more.

In each of the above embodiments, the percent decrease or fold-change may also be expressed as a range. For example, the decrease may be between about 10% and about 50%, between about 25% and about 75%, between about 50% and about 100%, between about 75% and about 125%, between about 1-100 fold, about 1-10 fold, about 1-5 fold, about 1-4 fold, about 1-3 fold, or about 1-2 fold.

Alternatively, the decrease may be between about 10% and about 30%, between about 20% and about 40%, between about 30% and about 50%, between about 40% and about 60%, between about 50% and about 70%, between about 60% and about 80%, between about 70% and about 90%, or between about 80% and about 100%.

(f) Ischemia/Reperfusion Injury

In an aspect, the present disclosure encompasses a method of mitigating an ischemia/reperfusion injury in a subject in need thereof. The method comprises administering a lipid emulsion composition as described herein. Non-limiting examples of ischemia/reperfusion injury may include cardiac dysfunction after cardiopulmonary bypass, PCTI (angioplasty and stent, where you open up coronary occlusion and re-establish blood flow to an ischemic part of the heart) or after return of spontaneous circulation (ROSC) after cardiac arrest or sudden death. As used herein, ischemia/reperfusion injury may refer to either reversible or irreversible injury (e.g. cell death).

An important example of reperfusion injury (that is, ischemia-reperfusion injury) occurs during reperfusion of heart after transitioning off of cardiopulmonary bypass typically used for open heart surgery (e.g., valve replacement, coronary bypass grafting or cardiac transplantation.) The reperfusion and associated reperfusion injury and reversible myocardial dysfunction (ie, 'stunning') occur when the aortic cross-clamp is removed from the ascending aorta allowing arterial blood to flow into the coronary arteries.

(g) Shock

One aspect of the present disclosure is a method of improving cardiac function in a patient in shock, wherein the patient has been administered at least one dose of a vasopressor or intotrope, the method comprising intravenously administering a lipid emulsion as described above. Another aspect of the present disclosure is a method of improving organ perfusion in a patient in shock, wherein the patient has been administered at least one high dose of a vasopressor, the method comprising intravenously administering a lipid emulsion as described above. Still another aspect of the present disclosure is a method of improving blood pressure in a patient in shock, wherein the patient has been administered at least one high dose of a vasopressor, the method comprising intravenously administering a lipid emulsion as described above.

Methods of diagnosing shock in a patient are known in the art. The sine qua non of shock state includes indications of reduced organ perfusion and corresponding poor or declining organ function, elevated blood lactate levels, and low cardiac output with hypotension requiring vasopressor or inotropic support which may include norepinephrine, epinephrine, phenylephrine, dopamine, dobutamine, vasopressin, or isoproterenol. As used herein, "high dose" means within 20% of the maximal dose recommended by the FDA for the particular vasopressor in question. Such doses are readily available to those of skill in the art. Improved organ perfusion is generally attended by increased arterial pressure (mean or systolic) and increased mixed central venous oxygen saturation, along with a reduced requirement for vasopressor or inotropic support. Blood lactate is elevated in reduced organ perfusion states and normalizes as organ perfusion improves. Improvement in organ perfusion is indicated by measures of specific organ function such as reduced plasma creatinine indicating improved renal function, or improved mental status for cerebral perfusion, reduced liver function tests for liver perfusion, improved skin color and temperature, etc.

In embodiments where cardiac function is improved, cardiac function may be measured by any accepted diagnostic parameter for cardiac function. In some embodiments, cardiac function may be measured by cardiac output and/or left ventricular ejection fraction (as measured by echocardiography), left ventricular diastolic pressure, or mixed central venous oxygen saturation. Generally speaking, a method of the present disclosure may encompass about a 5%, 10%, 15% or 20% improvement in cardiac function. In some embodiments, the improvement is at least 5, 6, 7, 8, 9, 10, 11, 12, 13, 14, 15, 16, 17, 18, 19, or 20% improvement. In embodiments where blood pressure is improved, blood pressure may be measured by any diagnostic means accepted in the art.

In certain embodiments, the present disclosure encompasses methods of reducing the therapeutic vasopressor dose required for a patient in shock, wherein the patient has been administered at least one high dose of a vasopressor. The method comprises intravenously administering a lipid emulsion as described above. As used herein, "reducing the vasopressor dose required" refers to reducing the total dose of vasopressor(s) needed to sustain blood pressure or total dose of inotropic support needed to sustain adequate cardiac output for the patient to recover from the shock episode compared to a patient that is not treated with a lipid emulsion.

(h) End-Stage or Refractory Heart Failure

The present disclosure encompasses methods of improving cardiac function in a patient diagnosed with end-stage heart failure. The method comprises intravenously administering a lipid emulsion as described above. In certain embodiments, the present disclosure also encompasses methods of improving blood pressure in a patient diagnosed with end-stage heart failure. The method comprises intravenously administering a lipid emulsion as described above. In particular embodiments, the present disclosure encompasses methods of improving organ perfusion in a patient diagnosed with end-stage heart failure. The method comprises intravenously administering a lipid emulsion as described above.

Methods of diagnosing end-stage heart failure are known in the art. In some embodiments, the end stage heart failure is decompensated heart failure. Refractory heart failure is heart failure that does not respond sufficiently to standard measures. In certain embodiments, a patient is a heart transplant candidate. Criteria for being a heart transplant candidate are known in the art. In particular embodiments, a patient is a candidate for extracorporeal membrane oxygenation (ECMO). In some embodiments, a patient is a candidate for a left ventricular assist device (LVAD).

(i) Myocardial Stunning

The present disclosure encompasses methods of improving cardiac function, blood pressure, or organ perfusion in a patient diagnosed with myocardial stunning or reversible cardiac dysfunction associated with reperfusion injury. The method comprises administering a lipid emulsion as described above. Methods of diagnosing myocardial stunning are known in the art. In certain embodiments, the lipid emulsion can be used to treat myocardial stunning that may occur after a cardiac transplant.

(j) Blood Sampling/Withdrawal

In certain aspects, a composition of the present disclosure may be used to mitigate a blood pressure drop that occurs after one or more blood samples are withdrawn from a subject, or during or after blood loss that occurs as a result of surgery. Such methods comprise administering a lipid emulsion composition of the invention prior to surgery or prior to withdrawing the one or more blood samples. The lipid emulsion may be administered from about several hours to about several minutes prior to blood withdrawal. For instance, the lipid emulsion may be administered from about 5, 10, 15, 20, 25, 30, 35, 40, 45, 50, 55, or 60 min prior to surgery or prior to blood withdrawal. Alternatively, the lipid emulsion may be administered from about 1, 2, 3, 4, 5, 6, 7, or 8 hours prior to blood withdrawal.

(j) Combinations

In some embodiments, a lipid composition of the present invention may be administered in combination with another active agent. When a lipid composition is combined with another active agent, the additional active agent may be dissolved in the aqueous portion of the lipid emulsion, or in the oil portion of the emulsion, depending on whether the additional agent is hydrophilic or hydrophobic.

In one embodiment, a lipid composition described herein may be administered in combination with an inotrope and/or other compound such as vitamin K or CoQ10 that can act as an electron acceptor and thereby improve tissue redox state, or improve mitochondrial function and metabolism including oxidative phosphorylation.

III. Methods of Addressing Drug Toxicity

In some embodiments, the present disclosure provides a method of treating systemic drug toxicity in a subject in need thereof, the method comprising intravenously administering to a subject a therapeutically effective amount of a lipid emulsion composition of the present disclosure. A composition of the present disclosure, with reduced particle size, presents an increased surface area and therefore increased capacity for transporting offending drug away from tissue targets. For instance, a lipid emulsion of the present disclosure may be used to treat toxicity associated with lipophilic or amphiphilic agents including tricyclic antidepressants (e.g., amitryptiline), adriamycin, organic solvents, local anesthetics, (e.g., bupivacaine, ropivacaine, mepivacaine, lidocaine, articaine, chloroprocaine, cocaine, etc.) and alcohol. Toxicity associated with additional agents, such as those detailed in Cao et al (2015) 48(3):387-397, hereby incorporated by reference, may also be treated by a lipid composition described herein. In some embodiments, drug toxicity may result in hypotension in a subject, which may be treated as detailed above for severe hypotensive episodes.

The methods and compositions of the present invention are applicable to several clinical scenarios in addition to treatment of acute toxicity. For example, in the situation where a patient will be receiving a known amount of toxin (e.g., a lipophilic chemotherapeutic agent such as adriamycin), an emulsion according to the invention may be administered to the patient to reduce toxicity of the agent thereby increasing its safe dose. In preferred embodiments, the lipid emulsion is administered after the adriamycin is administered.

In another scenario, when an acutely ill patient presents with apparent toxicity or a possible overdose of a known or unknown drug or drugs, e.g., presenting with cardiac arrhythmias in a young, otherwise healthy person, or a person with a history of depression being treated with tricyclic antidepressants, the patient may be treated with an emulsion according to the present invention.

Other exemplary lipophilic toxic agents which may be sequestered using the emulsions of the present invention include gasoline, inhaled propellants, and N,N-diethyl-m-toluamide (DEET).

The amount of toxin might be known precisely, or entirely unknown. In the latter case, the patient's clinical status (mildly or severely ill) will guide treatment. The length of treatment following an initial dose will be determined by clinical response against a predetermined maximum safe dose for a patient's weight, which is readily determined by routine methods. The spent emulsion will be metabolized slowly (over hours) probably by lipoprotein lipase which releases the fatty acids from the triglycerides. The toxin is then released from the emulsion droplets, but this slow release allows the patient's normal metabolism to chemically modify, excrete, or otherwise detoxify the toxin. The emulsion can be delivered via any peripheral or central vein.

EXAMPLES

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that changes may be made in the specific embodiments that are disclosed and still obtain a like or similar result without departing from the spirit and scope of the invention. Therefore, all matter set forth or shown in the accompanying drawings is to be interpreted as illustrative and not in a limiting sense.

The following examples illustrate various iterations of the invention.

Example 1

A lipid emulsion of the present disclosure containing 20% and 24% lipid is manufactured. Particle diameter and surface area (SA) of a prior art 20% lipid emulsion (row 1) is compared to the lipid emulsions of the example (row 2-3). The 20% lipid emulsion of the present disclosure has an increase in surface area for each droplet that is 43.5% greater than the prior art lipid emulsion.

TABLE A

| % lipid (g/100 mL) | Diameter (nm) | SA per 100 mL ($\times 10^2 m^2$) | Zeta potential |
|---|---|---|---|
| 20% | 330 | 4.00 | −45 mV |
| 20% | 230 | 5.74 | −57.4 mV |
| 24% | 230 | 6.89 | Not determined |

Example 2

A lipid emulsion of the present disclosure containing 24% lipid was manufactured. (Of note—the same manufacturing protocol may be used to create an emulsion with 20% lipid, specifically, the amount of lipid would be decreased from 24% to 20% while the water would be analogously increased.) In this prep, sodium hydroxide 0.1 M was included at 36 ml to reach a higher pH value for the emulsion. Additionally, a homogenization pressure of about 1600 atm was used to support reduction of mean globule size, already obtained in a previous trial. Recirculation time was adjusted to guarantee at least 6 homogenization cycles. Furthermore, the $N_2$ pressure used during homogenization was 1.0 atm.

TABLE B

| BATCH COMPOSITION | | |
|---|---|---|
| Raw material description | Amount per batch | Percentage values |
| Sojabean Oil, refined | 450.00 g | 24.00% |
| Purified Egg Phosphatide | 28.12 g | 1.50% |
| Glycerol Anhydrous | 35.62 g | 1.90% |
| NaOH 0.1M solution (~36 ml) | 36.00 g | 1.60% |
| W.F.I. | 1,325.26 g | 71.00% |
| Total | 1,875.00 g | 100.00% |
| $N_2$ gas for blowing, (for Homogenization only) | 1.0 atm | n.a. |

Pre-Emulsion Preparation
Oil Phase

In a glass beaker of 600 ml capacity, the Sojabean oil is added with continuous stirring (rotating turbo stirrer, (Silverson)) and subsequently the purified egg phosphatides. After the egg phosphatides are added, the oil phase is kept under continuous and homogeneous stirring, (approx. 1800-2200 rpm) and the oil phase is heated approx. to 62-64° C. to support the complete dissolution of the egg phospholipid.

When the egg phosphatides are completely dissolved in the Sojabean Oil, the solution is maintained for approx. 20' under homogeneous stirring and light blowing with $N_2$, to minimize the $O_2$ presence in the oil phase. (Solution 1)

Aqueous Phase

In a glass beaker of 3 lt capacity, are mixed homogeneously Glycerol, W.FI. and a 0.1M solution of Sodium Hydroxide to adjust pH, (approx. 10.2-11.2). The aqueous phase is heated approx. to 70° C. and it is maintained under light and constant blowing of $N_2$, in order to minimize the $O_2$ presence inside in the solution. (Solution 2)

Pre-Emulsion

At the end of the homogenization process, the temperature is manually cooled to 25°–28° C. and the pressure is gradually reduced to about 40 Kg/cm². When these conditions are reached, the final emulsion is transferred to the storage container under $N_2$ blowing. The pH value of the final emulsion at the end of homogenization process should be between 9.2 and 9.6. (Final Emulsion).

Filling and Sterilization

Using the final emulsion, 50 ml vials are manually filled and crimped, (vials are internally siliconized); during the manual filling operations the emulsion must be maintained under $N_2$ blowing. The filled vials are subsequently sterilized at 121° C. in an infeed autoclave. Mean globul size and pH may be verified, along with other potential indicators of degradation (ex. free fatty acids, phsphatidylcholine etc.).

Using the above protocol, the following compositions have been prepared:

| CP 01 - Rescue 24% | Trials data and results | | | | |
|---|---|---|---|---|---|
| Reference parameters | A | B | C | D | E |
| M-Gaulin pressure in bar | 1600 | 1600 | 1600 | 1200 | 1600 |
| M.G.S. sterilized emul. (nm) (measure of mean particle size) | 310 | 329.8 | 1035.4 | 823.6 | 316 |
| Purified Egg Phosphatide | 1.5% | 0.94% | 2.8% | 2.8% | 2.1% |

| CP 01 - Rescue 20% | Trials data and results | |
|---|---|---|
| Reference parameters | F | G |
| M-Gaulin pressure in bar | 1600 | 1200 |
| M.G.S. sterilized emul. (nm) (measure of mean particle size) | 278 | 278 |
| Purified Egg Phosphatide | 2% | 2% |

The Solution 1 is added to a beaker that already contains Solution 2. This operation is important for obtaining a "coarse emulsion", where all components, from oil and aqueous phases, are mixed together in the right stoichiometric ratio. The coarse emulsion is kept at 68-72° C., for 20 minutes under continuous stirring, (2800-3000 rpm), to support the complete and homogeneous mixing of all components. The pH value of the coarse emulsion should to be between 9.4 and 10.4. (Coarse Emulsion).

Final Emulsion Preparation

Micro-Homogenizer Set-Up

The laboratory equipment used for homogenization, called Montan-Gaulin, (2 lt. capacity), is adjusted, with the following working parameters:

homogenization step 2: 160 Kg/cm²
homogenization step 1: 1550-1600 Kg/cm²,
recirculation time: adjusted to guarantee at least 6 cycles during the emulsification process,
homogenization temperature, during the process is maintained between 60° C. and 64° C., and
$N_2$ blowing: the overpressure is kept between 1.0 and 1.1 Kg/cm².

Homogenization Process

The coarse emulsion, obtained at the end of pre-emulsification phase, is quickly transferred into the homogenizer to complete the homogenization process. The Montan-Gaulin equipment is adjusted to automatically maintain the working parameters described above.

Of note, in trials C and D, the mean particle size is too large to be compatible with an emulsion. This is attributed to the 2.8% emulsifier.

Example 3

Experiments were performed to demonstrate the improved performance of a lipid composition of the present disclosure in a rat model of drug toxicity. The response of blood pressure in the intact anesthetized rat after 10 mg/kg bupivacaine is delivered intravenously over 10 sec followed by the infusion of 4 mL/kg of either Intralipid 20% or a composition of the present disclosure was determined. The time to recover baseline blood pressure was 3 minutes for the Intralipid composition (FIG. 1B) and only 40 sec (FIG. 1A) for a composition of the present disclosure. The responses were so different that different scales had to be used for FIG. 1A and FIG. 1B. This is evidence that a composition of the present disclosure with a greater surface area accelerates recovery from drug toxicity. Arterial pressure is an indication of the degree of toxicity caused by bupivacaine, a local anesthetic which for these purposes serves as a canonical cause of cardiac pharmacotoxicity. Thus the accelerated recovery of arterial blood pressure indicates accelerated resolution (or reversal) of drug toxicity. That is, the emulsion of the present disclosure is a better antidote to drug overdose than prior art emulsions, such as Intralipid.

Example 4

Figure 2C:
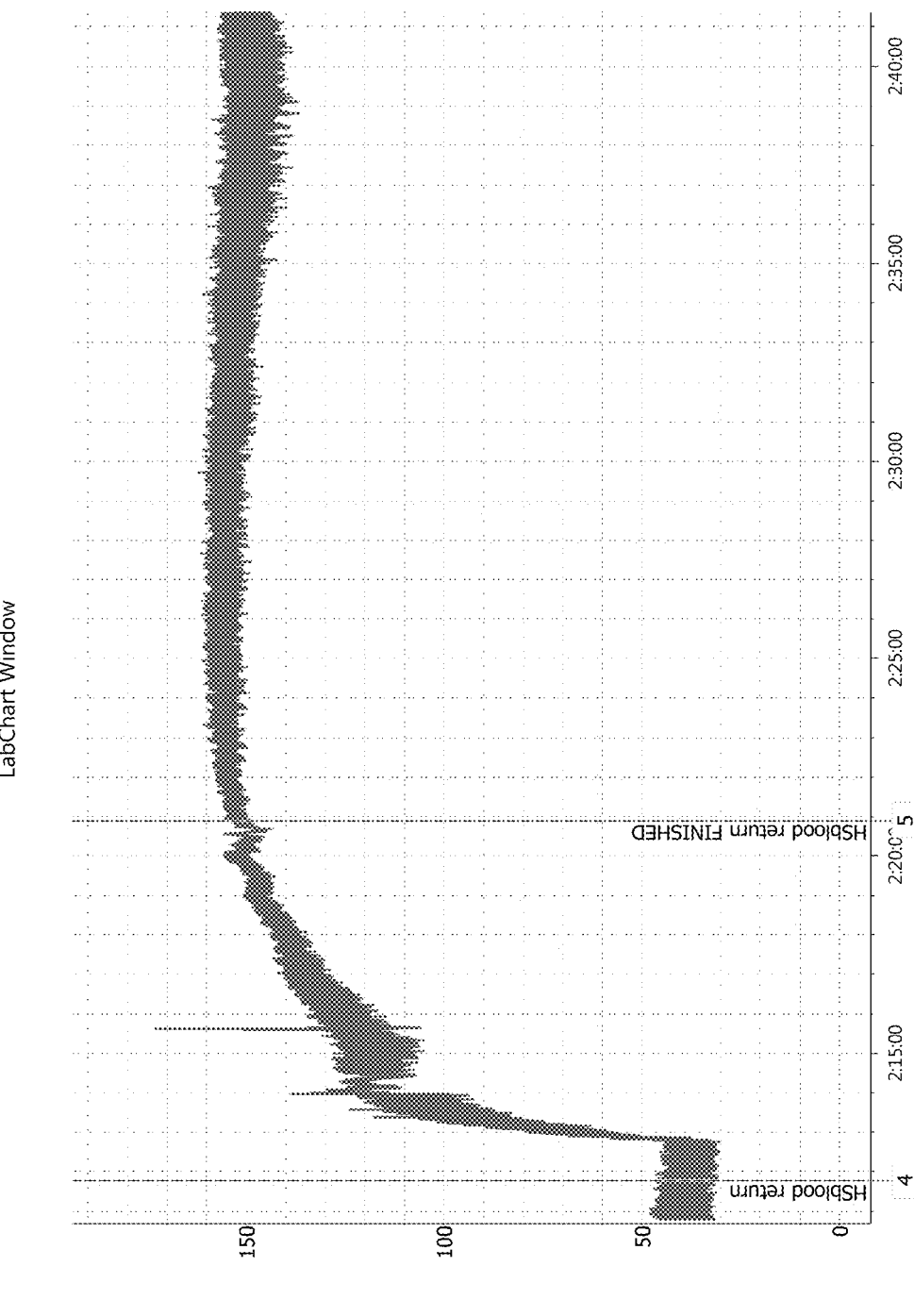
Figure 2D:
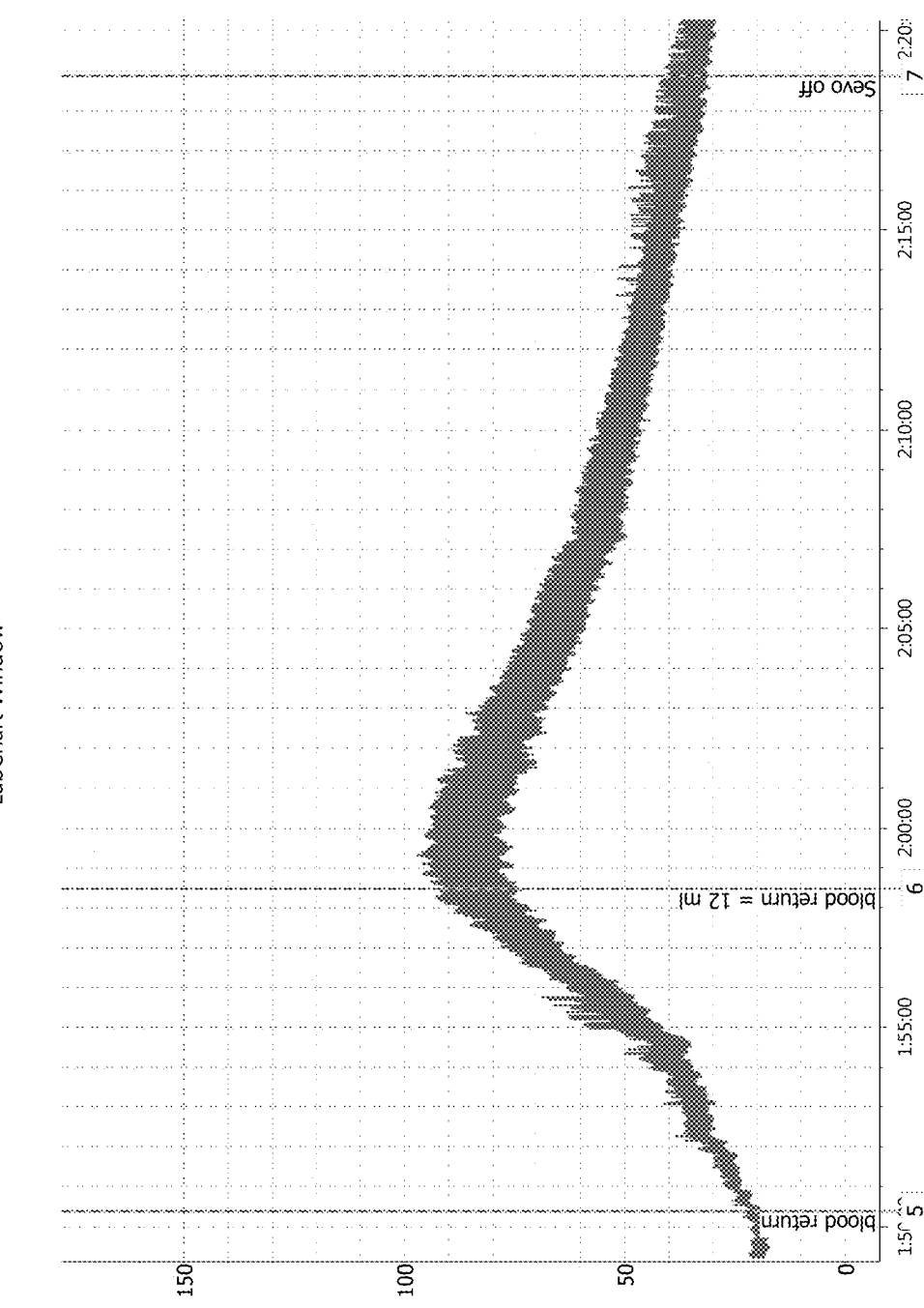

A model of hemorrhagic shock is performed in the intact, anesthetized, heparinized rat using sevoflurane 2.5% in 100% oxygen delivered continuously by mechanical ventilator via an endotracheal tube. One central venous catheter is placed for removing and delivering blood and one carotid arterial cannula is placed for continuous measurement of arterial pressure. The animals are pretreated with 9 mL/kg of either lipid emulsion of the present disclosure or saline delivered intravenously over 1 minute. After 15 minutes the initial hemorrhagic challenge is made by removing 25 mL/kg (11 mL) blood which drops the MAP to approximately 30 mmHg. The blood pressure is then allowed to recover spontaneously and the removed blood is rocked continuously in a syringe and maintained at 37 C. After 30 minutes of recovery a second hemorrhagic challenge is made by removing an additional 4 mL of blood, bringing the MAP again to 30 mm Hg. The entire amount (approximately 15 mL, total) of blood is then returned to the rat over 5-10 minutes and blood pressure is monitored for another 40 minutes. The key metrics are MAP during A) spontaneous recovery from the initial hemorrhagic challenge and B) response to blood transfusion after the second challenge. No vasopressors are administered during the experiment. FIG. 2 shows that the recovery of MAP in the saline pretreated rat (FIG. 2B) is incomplete compared with that of the rat given lipid emulsion prior to hemorrhage (FIG. 2A); and the response of MAP to blood transfusion in the saline pretreated rat (FIG. 2D) is transient compared to that of the lipid pre-treated rat whose pressure response is complete and sustained (FIG. 2C).

These experiments show that lipid pre-treatment improves both spontaneous recovery from hemorrhage as might occur during surgery and the response to blood transfusion as would be used in treating a patient with severe, intraoperative blood loss. Thus, lipid pre-treatment has the benefit of improving the recovery of blood pressure both spontaneously and in response to transfusion after profound blood loss. This apparent increase in resistance to hemorrhagic shock implies that pre-treating with lipid could reduce the need for using vasopressors and diminish the need for a blood transfusion or diminish the required volume of blood transfusion and most importantly, improve patient outcomes overall following major blood loss. The pretreatment with lipid emulsion also prevents capillary leak syndrome seen after return of blood following prolonged hemorrhagic shock in the saline-treated animals. This can be attributed to prevention of ischemia-reperfusion injury to capillary endothelial cells that allows the capillaries to remain intact.

What is claimed is:

1. A lipid emulsion composition suitable for intraoperative administration consisting of at least 20 percent (w/v) lipid, about 1 to about 5 percent (w/v) emulsifier, about 1 to about 5 percent (w/v) tonicity modifier, optionally an inotrope, and water, wherein particles of the lipid emulsion have an average particle diameter of about 200 nm to less than 230 nm, and wherein the particle size standard deviation is about 150 nm or less.

2. The composition of claim 1, wherein the composition comprises about 24 percent (w/v) lipid.

3. The composition of claim 1, wherein at least 50% of the particles have a particle diameter less than 250 nm.

4. The composition of claim 3, wherein at least 60% of the particles have a particle diameter less than 250 nm.

5. The composition of claim 4, wherein at least 70% of the particles have a particle diameter less than 250 nm.

6. The composition of claim 5, wherein at least 75% of the particles have a particle diameter less than 250 nm.

7. The composition of claim 1, wherein at least 50% of the particles have a particle diameter of about 240 nm or less.

8. The composition of claim 1, wherein at least 50% of the particles have a particle diameter of about 230 nm or less.

9. The composition of claim 1, wherein at least 90% of the particles have a particle diameter less than 250 nm, and at least 50% of the particles have a diameter of about 240 nm or less.

10. The composition of claim 1, wherein the average particle diameter of the composition changes by 25% or less following storage at 25° C. for 3 months.

11. The composition of claim 1, wherein the particle size standard deviation is about 75 nm or less.

12. The composition of claim 1, wherein the particle size standard deviation is about 25 nm or less.

13. The composition of claim 1, wherein the particles have an increased surface area as compared to the particles of a composition having the same mass having an average particle diameter of 330 nm.

14. The composition of claim 1, wherein the particles have a more negative zeta potential as compared to a composition having an average particle diameter of 330 nm.

15. The composition of claim 14, wherein the particles have a zeta potential of −57.4 mV.

16. The composition of claim 1, wherein the lipid is soybean oil, avocado oil, flaxseed oil, coconut oil, cottonseed oil, squalene oil, groundnut oil, olive oil, canola oil, corn oil, rapeseed oil, safflower oil, sunflower oil, an animal oil, fish oil, flavor oil, water insoluble vitamins, mineral oil, or any combination thereof.

17. The composition of claim 1, wherein the emulsifier is a synthetic lecithin comprising dihexanoyl-L-a-lecithin, or a phospholipid chosen from phosphatidylcholine, phosphatidylethanolamine, phosphatidylserine, phosphatidylinositol, phosphatidylglycerol, phosphatidic acid, lysophospholipids, egg or soybean phospholipid or combinations thereof and the emulsifier may be in any form, including salted or desalted, hydrogenated or partially hydrogenated, or natural, modified, semisynthetic or synthetic.

18. The composition of claim 1, wherein the tonicity modifier is glycerin, sorbitol, a polyoxyethylated hydrocarbon, a $C_6$-$C_{20}$ saturated aliphatic acid, or a $C_6$-$C_{20}$ unsaturated aliphatic acid.

19. The composition of claim 1, wherein the lipid is soybean oil, the emulsifier is egg yolk phospholipids, and the tonicity modifier is glycerin.

20. The composition of claim 1, wherein the lipid emulsion has a pH between about 4 to about 10.

21. The composition of claim 1, further comprising an inotrope.

22. The composition of claim 21, wherein the inotrope is selected from the group consisting of insulin, glucose, levosimendan, epinephrine, neosynephrine, norepinephrine, dobutamine, dopamine, and combinations thereof.

23. A lipid emulsion suitable for intravenous administration consisting of at least 20 percent (w/v) lipid, about 1 to about 5 percent (w/v) emulsifier, about 1 to about 5 percent (w/v) tonicity modifier, optionally an inotrope, and water, wherein particles of the lipid emulsion have an average particle diameter of about 200 nm to less than 230 nm.

* * * * *